(12) United States Patent
Gorinshteyn

(10) Patent No.: US 8,591,960 B2
(45) Date of Patent: Nov. 26, 2013

(54) COMPOSITION AND METHOD FOR TREATING BEDSORES, CUTS AND BURNS

(76) Inventor: Boris Gorinshteyn, Roswell, GA (US)

( * ) Notice: Subject to any disclaimer, the term of this patent is extended or adjusted under 35 U.S.C. 154(b) by 558 days.

(21) Appl. No.: 12/386,695

(22) Filed: Apr. 21, 2009

(65) Prior Publication Data

US 2009/0263500 A1      Oct. 22, 2009

Related U.S. Application Data

(60) Provisional application No. 61/125,139, filed on Apr. 22, 2008.

(51) Int. Cl.
*A61K 36/00* (2006.01)
*A61K 36/71* (2006.01)
*A61K 36/258* (2006.01)
*A61K 36/886* (2006.01)

(52) U.S. Cl.
USPC ............ 424/725; 424/726; 424/728; 424/744

(58) Field of Classification Search
None
See application file for complete search history.

(56) References Cited

U.S. PATENT DOCUMENTS

| | | | | |
|---|---|---|---|---|
| 5,266,318 | A * | 11/1993 | Taylor-McCord | 424/744 |
| 6,964,782 | B1 * | 11/2005 | Smith et al. | 424/616 |
| 2002/0034553 | A1 * | 3/2002 | Zayas | 424/614 |

OTHER PUBLICATIONS

Skidmore-Roth, L. Mosby's Handbook of Herbs & Natural Supplements. 2006 (3rd Edition) pp. 29-35, 517-523, 805-809.*
Duke, JA, et al. Handbook of Medicinal Herbs. 2002 (2nd Edition) p. 22.*
S. Foster & J.A. Duke, A Field Guide to Medicinal Plants: Eastern and Central North America, 1990, pp. 325-355 (index), Houghton-Mifflin, US.
L. Bremness, Herbs, 1993, cover & pp. 294-303 (index), DK Publishing, Great Britain.
Z.D. Draelos (ed.), Cosmeceuticals, 2005, pp. 5-10 (Chap. 1), 71-78 (Chap. 11); 79-88 (Chap. 12), Elsevier Saunders, US.

* cited by examiner

*Primary Examiner* — Daniel Sullivan
*Assistant Examiner* — Peter Anthopolos
(74) *Attorney, Agent, or Firm* — Denton Intellectual Property Law Firm LLC; F. Russell Denton

(57) ABSTRACT

The invention provides a composition and method to prevent and treat bedsores rapidly, efficaciously and economically. The composition comprises a novel combination of herbal extracts that has surprisingly synergistic and highly efficacious effects for the acceleration of wound healing, and which also disinfects and relieves pain in dermal wounds. The composition can also be used for the rapid healing of dermal burns and dermal cuts. The composition is comprised of extracts of aloe vera, passion flower, goldenseal, and American ginseng, and optionally includes ionic silver and mimosa extract. The treatment method comprises administering a fluid and or gel form of the composition to the wounded skin and or wound cavity therein as a prophylactic or therapeutic dose, and may be delivered by means of a wound dressing.

20 Claims, No Drawings

COMPOSITION AND METHOD FOR TREATING BEDSORES, CUTS AND BURNS

RELATED APPLICATION

This application claims priority to U.S. Provisional Patent Application No. 61/125,139, filed Apr. 22, 2008, entitled "Composition and Method for Treating Besores, Cuts and Burns," and incorporates by reference the contents of that application in its entirety.

FIELD OF THE INVENTION

The invention pertains to compositions and methods for healing wounds such as bedsores, pressure ulcers, lesions, cuts, and burns, and for the prevention of bedsores.

BACKGROUND

Bedsores, technically known as pressure ulcers or decubitus, are lesions caused by unrelieved pressure to any part of the body, especially over bony or cartilaginous areas. These sores are generally completely treatable if detected early, but without medical attention they can be fatal. Pressure sores can trigger other ailments, causing considerable suffering and financial cost. Brem, H., Kirsner, R. S., and Falanga, V., "Protocol for the successful treatment of venous ulcers," *Am. J Surgery*, 188(1 Supp. 1):1-8 (July 2004). Potential complications include autonomic dysreflexia, bladder distension, osteomyelitis, pyarthroses, sepsis, amyloidosis, anemia, urethral fistula, gangrene and very rarely malignant transformation. Sores often recur because patients do not follow recommended treatment or develop seromas, hematomas, infections, or dehiscence. Paralytic patients are the most likely people to have pressure sores recur. In some cases, complications from pressure sores can be life-threatening. The most common causes of fatality stem from renal failure and amyloidosis. As currently defined by the U.S. National Pressure Ulcer Advisory Panel (NPUAP), pressure ulcers have four recognized stages, as follows:

STAGE I: superficial, accompanied by redness that does not subside after pressure is relieved. This stage is visually similar to reactive hyperemia (i.e., excessive redness) in skin after prolonged application of pressure. Stage I pressure ulcers are distinguished from reactive hyperemia because: a) reactive hyperemia resolves itself within three quarters of the time over which pressure was applied, and b) reactive hyperemia blanches when pressure is applied, whereas a Stage I pressure ulcer does not. Stage 1 pressure ulcer skin may be hotter or cooler than normal, have an odd texture, or perhaps be painful to the patient. Whereas there is obvious redness on light-skinned patients, ulcers on darker-skinned individuals may be shades of purple or blue in comparison to lighter skin tones.

STAGE II: includes damage to the epidermis extending into but no deeper than the dermis. A stage 2 ulcer may be termed a blister or abrasion.

STAGE III: involves the full thickness of skin and may extend into subcutaneous tissue. The blood supply is relatively poor and can be difficult to heal. There may also be subsurface damage that is more extensive than appears on the surface.

STAGE IV: extends into the muscle, tendon or even bone.

UNSTAGEABLE pressure ulcers are those covered with dead cells (i.e., eschar) and exudate from the wound, such that the pressure ulcer depth cannot be determined.

Higher stage wounds require prolonged healing times. About 75% of Stage II ulcers heal within eight weeks. For Stage IV pressure ulcers only 62% ever heal, and only 52% heal within one year. Thomas, D. R., Diebold, M. R., Eggemeyer, L. M., "A controlled, randomized, comparative study of a radiant heat bandage on the healing of stage 3-4 pressure ulcers: A pilot study." *J. Am. Med. Dir. Assoc.*, 6(1):46-49 (January-February 2005). Counterintuitively, pressure ulcers do not regress in stage as they heal. A pressure ulcer that becomes shallower with healing is described in terms of its original deepest depth (e.g., a healing Stage II pressure ulcer).

Three forces account for bedsore etiology. First, Tissue compression arises from the force of bone against a surface, as when a patient remains in a single decubitus position for a lengthy period. This results in decreased tissue perfusion; ischemia occurs and can lead to tissue necrosis if left untreated in an immunocompromised patient. Second, shear forces arising in prolonged single decubitus positions result when the deep fascia and skeletal muscle slides down under the force of gravity, thus blood vessels can be pinched off and ischemia and tissue necrosis may occur. Finally, friction forces resist the shearing of skin, and thus can cause excess shedding of epidermal layers. The etiology may be aggravated by other conditions. Excess moisture from incontinence, perspiration or exudate may weaken adhesion between epithelial cells and thereby cause maceration of the epidermis. Age, malnutrition, vascular disease, diabetes mellitus and smoking are some other factors that can affect the etiology. The exact mechanism of etiology is not completely clear: it may be due to the injury of deep tissue that spreads outward to the epidermis, or possibly it may be due to a top-down deterioration that begins at the surface of the skin. Niezgoda, J. A., Mendez-Eastman, S. "The effective management of pressure ulcers," *Advances in Skin & Wound Care: The Journal for Prevention and Healing*, 19(1-Supp.):3-15 (2006).

The incidence of bedsores varies widely and depends in part on the type of care. For acute care, the range is 0.4% to 38% incidence. For long-term care it is 2.2% to 23.9%. For home care it is 0% to 29%. Intensive care units have higher rates (8% to 40%) because their patients are more often immunocompromised. NPUAP Board of Directors, "Pressure ulcers in America: prevalence, incidence, and implications for the future," in *An Executive Summary of the NPUAP Monograph*, ed. Cuddigan, J., et al., (July/August 2001), The risk of developing bedsores can be determined by using the Braden Scale for Predicting Ulcer Pressure Risk, using six categories: sensory perception; moisture; activity; mobility; nutrition; and friction and shear. The best possible score is 23; the worst is 6. For a total score below 11 the patient is at risk of developing bedsores. Jiricka, M K, Ryan, P, Carvalho, M A, and Bukvich, J, "Pressure ulcer risk factors in an ICU population," *Am. J. Crit. Care*, 4(5):361-367 (1995).

To date the effective healing of bedsores has typically required a multidisciplinary approach and teamwork among specialists along six lines of treatment. (see, e.g., Rothrock, J. C., *Alexander's Care of the Patient in Surgery*, 13$^{th}$ ed. (Mosby, 2007).

1. Debridement—necrotic tissue must be removed during treatment in order to minimize bacterial growth. Several methods are currently in use for debridement. Niezgoda, J. A., Mendez-Eastman, S., "The Effective Management of Pressure Ulcers." *Advances in Skin & Wound Care: The Journal for Prevention and Healing*, 19(1—Supp.): 3-15 (2006). These methods vary in effectiveness and speed, and some are painful. They include: the use of moist dressings to aid the body's own digestion enzymes (autolytic debridement); the use of medical maggots (biological debridement, see http:// www.fda.gov/cdrh/510k/sumjan04.html); tearing off dressings that are applied wet and removed when dry (mechanical debridement); scraping necrotic tissue off with a scalpel (sharp debridement); surgical removal (surgical debridement); and separation of necrotic and healthy tissue sonically (ultrasound-assisted wound therapy).

2. Infection control—to avoid breeding bacteria in purulent discharge, particularly in immunocompromised patients. Additional symptoms of systemic infection include fever, pain, erythema, oedema, and warmth of the area; infected wounds may also have a gangrenous smell, be discoloured, and eventually exude even more pus. Antiseptics and antimicrobials are typically applied immediately; experts advise against the use of hydrogen peroxide for this purpose due to its potential toxicity to the wound. Recently introduced wound dressings for this purpose have cadexomer iodine and silver in them. Duoderm is often used on smaller wounds to both provide comfort and protect them from outside air and infections. Systemic antibiotics are typically avoided when treating infection of a bedsore, because it can lead to bacterial resistance.

3. Diet—dietitians are often consulted to ensure that the patient ingests enough protein to ensure tissue repair. Lab tests for serum albumin and lymphocyte counts as well as bioelectrical impedance analysis are typical diagnostic tools. Nutritional supplementation may include but is not limited to, arginine, glutamine, vitamin A, vitamin B complex, vitamin E, vitamin C, magnesium, manganese, selenium and zinc, all under a physician's care to prevent the use of detrimental incorrect dosages.

4. Pressure relief—once a bedsore is found, pressure on it must be removed immediately and the patient turned at least once every two hours to avoid aggravating the wound. Nursing homes and hospitals usually have bedsore prevention programs employing a standing frame to reduce pressure, and ensure dry sheets by means of catheters or impermeable dressings. For paralyzed individuals, a pressure shifting schedule and pressure relief cushions can be effective. Pressure distributive mattresses can also be used. Methods to evaluate efficacy of these products were only recently developed. Bain, D. S., Ferguson-Pell, M. W., "Remote monitoring of sitting behaviour of people with spinal injury," *J. Rehab. Res. Dev.*, 39(4):513-520 (July 2002).

5. Caregiver education—especially for home-based care, a family must be educated about how to treat their loved one's pressure ulcers. The training includes among things the proper way to turn a patient, how to properly dress the wound, proper nutrition for the patient, and how to deal with crisis. Because of the difficulty psychological consultants for the home caregiver are sometimes recommended.

6. Wound intervention—this depends on the stage of the bedsore. Stage I and II ulcers are treated under the guidelines of the American Medical Directors Association (AMDA). Stage III and IV ulcers often receive surgery such as closure methods (e.g., tissue flap, skin graft) or topical negative pressure wound therapy by means of a foam that is held the wound cavity by a film with an airtight seal. Progress under negative pressure therapy is reevaluated every two weeks. Negative pressure therapy is contraindicated for patients who have not been prepared or had previous steps toward recovery, or where the wound has in inadequate circulation, is raw and debrided, has necrotized tissue and eschar, or is fibrotic. Topical ointments such as the zinc oxide-based Sensicure™ are also sometimes used, as are alcohol wipes, but these have not proved to be particularly effective in accelerating healing.

As is clear from the description above, the incidence of bedsores is widespread, these sores represent a great hazard to health, and not only have they healed very slowly at best, but they are both difficult and expensive to treat. There is, then, an ongoing need for therapies to prevent and treat bedsores in a rapid, thrifty and efficacious manner. Several types of cuts and burns present comparable challenges for clinical medicine, and there is an ongoing need for a treatment method that can accelerate their healing as well.

BRIEF DESCRIPTION OF THE INVENTION

The invention provides a composition and method to treat a variety of wounds rapidly, efficaciously and economically, and which are particularly useful for healing and preventing bedsores. The composition comprises a novel combination of herbal extracts which, when blended, manifest surprisingly synergistic and highly efficacious therapeutic effects, and which treat or prevent infection, relieve pain, and accelerate the healing of tissue. In addition to treating bedsores, the composition can also be used for the rapid healing of first, second and third degree burns, including sunburns and radiation burns. The composition can also be used for the accelerated healing of dermal cuts such as lacerations, abrasions, contusions, surgical incisions, and other cuts. The composition is comprised of extracts of aloe vera, passion flower, goldenseal, and American ginseng, and optionally includes mimosa extract and ionic silver.

The treatment method comprises administering a fluid and or gel form of the composition to the wounded skin or to a wound cavity therein as a prophylactic or healing treatment; for instance to prevent bedsores it can be applied to the area of the body where bedsores or pressure ulcers are most likely to form. In an exemplary embodiment of the invention a superficial burn wound is sprayed with the composition whenever pain returns to the patient, until the pain subsides. In another exemplary embodiment the composition is applied in the form of a wet medicated wound dressing for a period of several minutes once or twice daily as a prophylactic or until the wound is healed.

DETAILED DESCRIPTION OF THE INVENTION

NHF5 is a dermatological formula designed to substantially accelerate healing following dermal damage. It is aimed at remediation of burns, abrasions, lacerations, surgical incisions, contusions, and lesions. It has three primary pharmacological benefits—antiseptic, analgesic and catabolic. That is, it prevents infection, provides pain relief and, most importantly, accelerates the healing of tissue following wounding from any source. NHF5 is a singular and unique blend of natural ingredients never before combined for topical use. This combination is surprisingly synergistic in its therapeutic effects, and has a level of efficacy that is more commonly associated with synthetic compounds after they have been optimized through extensive pharmaceutical research and clinical trials. The benefit of the blend was initially discovered by the inventor during research on chemical decontamination therapies, when an early variant of the combination proved efficacious in the treatment of burns and cuts. Subsequent experimentation and reformulation led to the present optimized combination of extracts. The desired effect is acquired by combining antiseptic and analgesic capacities. The alkaloids in the formula appear to prevent the majority of bacterial infections. Their combination with hydrogen peroxide produces excellent cleansing and antiseptic capacity; current literature teaches against the use of hydrogen peroxide because of the difficulty of applying a proper dosage, however the current composition works quite well. And since the mixture does not leave any oily residues, the oxygen in the air combines with proteins in the mixture and provides amplified coagulation of the blood. Also, the specific analgesic used in the formula provides temporary relief of dermal discomfort.

The chemical balance in the NHF5 formula has been engineered to enable penetration of the epidermis so that the interstitial electrolyte balance can be reestablished. The profound effect of NHF5's electrolyte balancing action prevents the generation of edema. This substantial reduction of fluid accumulation in the interstitial space also accelerates the healing process by preventing separation of epidermal from endodermal tissue. A related issue is that ordinarily damaged dermal areas tend to produce keloidal or scar tissue. The catabolic extract used in NHF5 modifies regeneration such that tissue develops with a minimum of keloidal activity.

Catabolic Component

The catabolic component comprises American ginseng extract, assisted by extracts of aloe vera, goldenseal, and optionally mimosa. In traditional Chinese medicine American ginseng extract is considered a yin or cooling tonic herb that works through the lung, stomach and spleen channels to support the adrenal glands, balance metabolism and increase fluids. It is typically prescribed in cases of stress, asthma, mental fatigue, bronchitis, chronic fevers and weak or infected lungs. In a separate ethnobotanical development, numerous native American tribes have used this type of extract for a wide variety of applications, ranging from fever reduction and enhancement of mental faculties and female fertility to geriatric rejuvenation. Aloe vera extract aids healing and is a transdermal agent and moisturizer. Goldenseal extract is an immunostimulator; and its berberine alkaloids prevent bacterial infection. Passion flower extract is a relaxant and sleeping aid; and its extract also improves vasodilation and coagulation; populates tissue with sodium and potassium ions, prevents edema, reduces formation of keloid—i.e., scar tissue. Scars arise when fluid is released into interstitial spaces to dilute catecholamines, as sensed by pain receptors.

The catabolic American ginseng extract in NHF5 is considered an "adaptogen", or tonic herb that tends to normalize and strengthen metabolism and immunity over time. The American ginseng used in NHF5 is one of a group of herbs that practitioners of TCM use with different actions and indications including stimulation of nerve growth factor and RNA/DNA synthesis, modulation of neurotransmitter activity and blood sugar levels, and protection against myocardial ischemia. In addition, it may enhance macrophage activity, adrenal hormone production, tissue oxygenation, energy production, and capacity for work and stress. In a controlled study of persons over 60, this herb increased the ratio of superoxide-dismutase to lipid peroxides.

The known adaptogen constituents of NHF5 are triterpenoid saponins. The most common ones $R_{g1}$ and $R_{b1}$ have been studied extensively. In vitro $R_{g1}$ acts as mild nervous stimulant, and $R_{b1}$ acts as mild sedative, although these effects are dose-sensitive. This extract is particularly high in $R_{b1}$ and $R_{g1}$ does not contain $R_{b2}$ or $R_{g2}$ and often lacks R. Preferred roots offer a high ratio of $R_{b1}$ to $R_{g1}$.

The additional presence of polysaccharides (panaxans A-U), polypeptides, phytosterols (e.g., Betasitosterol), and essential oils and nutrients (e.g., selenium, Vitamin C, and Vitamins-B) may account for the wide range of effects displayed by these substances.

The catabolic effects of NHF5 may optionally be enhanced by combination therapy, alternation therapy, or some variant, by supplementing or augmention NHF5 with a complementary vasodilation stimulating compound such as nitroglycerin to improve circulation in the vicinity of a dermal wound. Because of nitroglycerin's systemic potency and affect on other parts of the body, when that compound is used with the present invention care must be taken to avoid applying substantial doses of nitroglycerin within a wound in a way that could lead to its migration into the circulatory system.

Antiseptic Component

The antiseptic component comprises goldenseal extract, optionally assisted by silver ion. Native Americans used the type of antiseptic extract found in NHF5 for a wide range of health conditions including topical inflammations, debility, dyspepsia, whooping cough, pneumonia, diarrhea, fever, and sour stomach. European settlers of the 18th century used it as a wash for eye inflammations. In the 19th and 20th centuries, the folk applications expanded to include inflammations and infections of the mucus membranes (e.g., canker sores and sore gums or throat), skin sores, bleeding, menstrual complaints, ulcers, gastritis, colitis, constipation, ringworm, acne, genitourinary infections, thrush, and snake bite.

Without being bound by theory, two of the natural products in NHF5, hydrastine and berberine, are thought to be the most antiseptically potent and they share many properties in common. Based on published clinical trials and experiments in vitro or in vivo, berberine sulfate is variably but effectively antibiotic against parasites, fungi, mycobacterium, and gram-negative or gram-positive bacteria, including *Streptococci, Staphylococci, Tuberde bacillus, Cholera vibrio, E. coli, Trichimonas, Leishmania, Entamoeba, Giardia, Trypanosoma*, and *Chlamydia*. Because berberine can kill gram negative bacteria, e.g., spirochetes, it is a more effective antiseptic than soap. Berberine also exhibits anti-tumor activity against malignancies of the human and rat brain, equivalent to the chemotherapeutic BCNU. This extract also has vasoconstrictive effect.

Isoquinoline alkaloids are the active constituents of the NHF5 formula, led by hydrastine (1.5-4%) and berberine (0.5-6%), with lesser amounts of related compounds, including canadine, canadat ME, 1-a-hydrastine, iso-hydrastine, (5)-corypatmine, berberastine, and 5 hydroxy-tetra-hydroberberine. This extract also contains chlorogenic acid, meconin, lipids (75% unsaturated fatty acids), resin, starches, and traces of volatile oil.

The form of silver used is important. The ionic form (i.e., Ag+) in water is not toxic to the body, whereas colloidal silver is. Also, silver ion kills bacteria on contact, and its antibiotic mechanism differs from that of the alkaloids.

Analgesic Component

The analgesic component employed in NHF5 comprises passion flower extract. It is native to the Americas, and was listed in the U.S. National Formulary until 1936. By 1986, it was widely used in the U.S. and Europe, typically in therapeutic compositions containing other sedative herbs (hawthorn, valerian, hops, Kava, etc.). Modern herbalists prescribe it as an antispasmodic agent for Parkinson's disease and tension-related asthma, and as an analgesic for nerve pain and shingles. In Europe, this type of extract is standardized for mono-C- and di-C-glycoside flavones and is commonly used to control abnormal heart rhythms.

Pharmacologically this extract produces analgesic and sedative-hypnotic effects in experimental rodents, as well as a temporary drop in blood pressure. Specifically, it depresses motor reflexes, reduces general activity levels, raises the pain threshold and reduces external signs of anxiety. To date, no clinical trials have been published for this extract.

The specific chemical components responsible for this agent's sedative effects are not completely known, because the chemistry of the plant has not been established exhaustively. The major components of the extract are flavone di-C- glycosides (isovitexin, schaftoside, orientin and their isomers), which are typically used as markers of plant identity and potency. However, these compounds possess no known sedative properties in themselves. This extract also contains harmala alkaloids, though most researchers discount the theory that one or more may play a major role in the plant's sedative effects. Maltol is also present and can produce sedative effects, but not separately at the doses typically encountered in extract itself.

Other Properties

An additional benefit of the new composition is its cosmetic appeal. Unlike a number of other terpene-containing herbal medicinal formulations, the color of NHF5 is a pleasant light green and is relatively invisible against the skin. Also, the formulation's odor is not pronounced. By contrast, chamomile extract, though effective at reversing the effect of some chemical damage to skin, has a brown color, and ceases to be effective when its terpene is decolorized for instance by chlorination. Moreover the terpenes of NHF5 are more potent than many other medicinal terpenes, such as those found in chamomile.

Indications

An important application for the formula is for the treatment and prevention of bedsores. This is a critical issue for patients with long-term hospitalizations and rehabilitations. The treatment has proven more effective to date than other treatment regimens. Because the composition provides three critical therapeutic benefits in one stable formula, and because the composition is easily dispensed in a variety of ways, it lends itself well to treating this and other indications.

A related valuable application for the formula is the treatment of epithelial and endothelial dysfunctions that occur in elderly patients who have a preexisting condition of Type III diabetes in combination with prolonged immobilization. For such patients the healing process is protracted because of abnormalities in tissue development due to diabetes; these can lead to severe infections and to hospitalization. Bed sores delay their recovery, and may be complicated by a reduced immune response to bacterial, viral, or fungal infections.

Alternative uses contemplated for NHF5 also include treatment of severe burns, and the composition has the potential to overshadow current treatment regimes. Anecdotal data finds that third degree burns may be treated with NHF5 in a way that reduces blistering, restores electrolyte balance, and undistorted cell development, and there is evidence that the action of NHF5 is superior to any reported treatment protocol for such burns. Third degree radiation burns in and individual have been treated in a way that restores the sub dermal and epidermal layers within 72 hours of treatment, eliminating swelling, reducing pain, and leaving virtually no scarring. This is particularly important for radiation therapy for cancer, because it facilitates more aggressive radiological treatments of bone and other malignancies where potential radiation burning has heretofore limited the oncologist's options.

A related indication is as a treatment for sunburn. With the ongoing depletion of atmospheric ozone, sunburn is likely to become a far more important medical and personal issue in the future. NHF5 has the capacity to prevent blistering, skin peeling, and pain that accompany severe burning.

Another application is the use of the formula as a post-surgical antiseptic. There is anecdotal evidence that the formula, while providing the same antiseptic values as current antiseptics, reduces edema and inflammation, and provides increased catabolic action. This can reduce hospital stays and enable patients to return to regular activities more quickly.

Some existing products on the market combine pharmacological benefits for the care of dermal wound. For instance Neosporin™ has both antiseptic and analgesic properties, and is used for dermal wounds. However, its catabolic action is limited. Anecdotal comparisons to date indicate that healing is more rapid with NHF5, presumably because of NHF5's ability to reduce edema and promote rapid tissue regeneration.

Uses are also contemplated particularly for dermal wounds associated with military medical trauma, the enhanced recovery speeds provided by NHF5 will be particularly valuable in this context.

Composition Ranges

The following composition ranges of dried extract weights relative to the whole weight of the liquid or gel formulation are found to be useful in various embodiments of NHF5 compositions.

For aloe vera: in one embodiment 0.15 to 40 weight %; in another embodiment 0.5 to 20 weight %; in a further embodiment 0.75 to 10 weight %; in yet another embodiment 1.0 to 5.0 weight %; in a different embodiment, 1.25 to 2.5 weight %; in an alternative embodiment 1.5 to 2 weight %; in still another embodiment about 1.7 weight %.

For dried extract of passion flower: in one embodiment 0.015 to 4 weight %; in another embodiment 0.05 to 2 weight %; in a further embodiment 0.075 to 1 weight %; in yet another embodiment 0.10 to 0.50 weight %; in a different embodiment, 0.125 to 0.25 weight %; in an alternative embodiment 0.15 to 0.20 weight %; in still another embodiment about 0.17 weight %.

For dried extract of goldenseal: in one embodiment 0.015 to 4 weight %; in another embodiment 0.05 to 2 weight %; in a further embodiment 0.075 to 1 weight %; in yet another embodiment 0.10 to 0.50 weight %; in a different embodiment, 0.125 to 0.25 weight %; in an alternative embodiment 0.15 to 0.20 weight %; in still another embodiment about 0.17 weight %.

For dried extract of American ginseng: in one embodiment 0.03 to 8 weight %; in another embodiment 0.1 to 4 weight %; in a further embodiment 0.15 to 2 weight %; in yet another embodiment 0.20 to 1.0 weight %; in a different embodiment, 0.25 to 0.50 weight %; in an alternative embodiment 0.30 to 0.40 weight %; in still another embodiment about 0.34 weight %.

For dried extract of mimosa: in one embodiment 0 to 8 weight %; in another embodiment 0.015 to 4 weight %; in another embodiment 0.05 to 2 weight %; in a further embodiment 0.075 to 1 weight %; in yet another embodiment 0.10 to 0.50 weight %; in a different embodiment, 0.125 to 0.25 weight %; in an alternative embodiment 0.15 to 0.20 weight %; in still another embodiment about 0.17 weight %.

In one embodiment NHF5 composition comprises an organic solvent selected from the group consisting of methanol, ethanol, iso-propanol, n-propanol, tert-butanol, sec-butanol, n-butanol, dimethylsulfoxide, n-methylformamide, 1,2,3-propanetriol, 1,2-propanediol, and 1,2-ethanediol.

In one embodiment ethyl alcohol (i.e., when its molecular water content is factored out) represents 0 to 85 volume % of the aggregate volume of the liquid components of NHF5; in another embodiment it represents 2 to 50 volume %; in a further embodiment it represents 3 to 25 volume %; in yet another embodiment it represents 4 to 10 volume %; in an alternative embodiment it represents 6 to 8 weight %; in still another embodiment it represents about 6.6 volume % of the aggregate volume of the liquid components of NHF5.

In one embodiment hydrogen peroxide (i.e., when its molecular water content is factored out) represents 0.03 to 3.0 volume % of the aggregate volume of the liquid components of NHF5; in another embodiment it represents 0.06 to 1.5 volume %; in a further embodiment it represents 0.09 to 0.75 volume %; in yet another embodiment it represents 0.12 to 0.3 volume %; in an alternative embodiment it represents 0.18 to 0.24 weight %; in still another embodiment it represents about 0.2 volume % of the aggregate volume of the liquid components of NHF5.

In one embodiment water represents 0 to 99.97 volume % of the aggregate volume of the liquid components of NHF5; in another embodiment it represents 50 to 99 volume %; in a further embodiment it represents 80 to 98 volume %; in yet another embodiment it represents 90 to 97 volume %; in an alternative embodiment it represents 92 to 96 weight %; in still another embodiment it represents about 94 volume % of the aggregate volume of the liquid components of NHF5.

In one embodiment silver ion is present in the NHF5 composition in the range 0-1000 ppm; in another embodiment it is present in the range 2-200 ppm; in a different embodiment it is present in the range 5-50 ppm; in a further embodiment it is present in the range 7-20 ppm; in still another embodiment it is present at about 10 ppm.

Definitions

The term "treatment" as used herein refers to medical treatment; whether the treatment is therapeutic or prophylactic depends upon the context of the use.

The term "therapeutic" as used herein with respect to a wound refers to a treatment for the healing of that wound.

The terms "prophylactic" and "preventive" as used herein are synonymous and refer to a treatment to prevent formation of lesion.

The term "wound dressing" as used herein refers to a bandage, cloth, or other artifact placed on a wound to protect it or to deliver a pharmaceutical composition. When the text herein mentions "wetting" a wound dressing with a pharmaceutical composition, it refers to applying a liquid or gel composition to the surface or weave of a wound dressing in order to transfer the composition to a patient's wound.

The term "extract" as used herein has its normal and ordinary meaning in the art of medicinal herbal compositions. The term "dried extract" as used herein refers to an extract from which extracting liquids such as water, alcohol and or another extracting liquid have been removed.

The term "silver ion" as used herein refers to the cation $Ag^+$, as opposed to silver in its zero-valent state.

EXAMPLE 1

Illustrative Preparation of NHF5 Composition

The following is an illustrative embodiment of a composition made according to the present invention. The upper end of useful ranges for weight % incorporation of each extract is largely determined by their solubility, while the lower end is determined by the efficacy at that concentration. The choice of organic solvent and the ratios of the liquid ingredients is likewise variable. The specific formulation shown below has been found to be particularly useful but the invention is not so limited.

| Dry Ingredients | Dry Weight Basis: | Exemplary Range: |
|---|---|---|
| Dried extract of *Aloe Vera* (pure) | 250 g | 25 g-5000 g |
| Dried extract of Passion Flower (PE 4%) | 25 g | 3 g-500 g |
| Dried extract of Goldenseal (PE 5%) | 25 g | 3 g-500 g |
| Dried extract of American Ginseng (PE 5%) | 50 g | 5 g-1000 g |
| Dried extract of *Mimosa* Extract (PE 4%) (optional) | 25 g if present | 3 g-3000 g |

Optional gelling agent, in amount sufficient to gel 4 gallons of water to desired level of firmness.

| Liquid Ingredients | Volume Basis: |
|---|---|
| Ethyl Alcohol | 1 liter (90% EtOH, 10% $H_2O$) |
| Hydrogen Peroxide | 1 liter (3% $H_2O_2$, 97% water by weight) |
| Water (Purified) optionally with $Ag^+$ | Bring total volume to 4 gallons |

The extracts were obtained in pharmaceutical grade from NatureX (375 Huyler St., South Hackensack, N.J. 07606 (201) 440-5000), with a chromatograph for each batch. The extracts of aloe vera and of mimosa are quite water soluble. The passion flower extract is the least water-soluble of the extracts, and is made more soluble by the inclusion of an organic solvent such as ethyl alcohol. The extracts of passion flower, goldenseal and ginseng in the amounts shown here are approximately fully soluble in 800 mL of water. The extracts used here contained a small amount of fibrous matter from the plants that were the source of the extract; this fibrous matter did not dissolve.

Silver cation, to the extent it was included, was here provided by the dissolution of trace amount from silver spheres. The spheres were comprised of 340 grams of 99.999% pure hollow silver spheres held by mesh in a plastic tube having length 5 inches and diameter 2 inches. The silver spheres are about 6 mm (¼ inch) in diameter, have 0.36 mm wall thicknesses and two 1 mm (ca. 1/24 inch) diameter circular openings in the walls at opposite points in each sphere. Water that had been pre-purified by reverse osmosis was pumped through the plastic tube at the rate of 1 gallon per minute at room temperature (22° C.) by a small, hand-held electric pump. The exact concentration of Ag+ ion obtained this way in water is uncertain and probably varies, but empirically it is high enough to be antibiotic and is likely to be present at a few dozens of ppm. Some trace of divalent and monovalent metal ions ($Na^+$ and $Ca^{++}$) also remained in the water. However the invention is not limited to use with this particular method of generating silver cation, or to the concentration ranges of silver ion employed here.

The gelling agent is optional, and may be a natural material such as protein gelatin, guar gum, carrageenan, or another natural gum, or may be a synthetic or quasi-synthetic materials such as polyethylene oxide, methyl cellulose or hydroxypropyl methylcellulose. Many suitable materials, concentrations and conditions for formulating and gelling aqueous compositions are well known to persons having ordinary skill in the art of gel manufacture.

EXAMPLE 2

Treating Bedsores

The composition is used as a cleansing agent and leave fluid soaked bandages on the affected areas for twenty to thirty minutes at a time. Use this regimen as often as ordinary procedures require cleaning bedsores. In an illustrative protocol for a stage 1 bedsore, NHF fluid is applied to a clean bandage and bandage is attached to the affected area continuously for a period of 20 min. The application is repeated once daily for a total of 5 treatments.

In a particular example, a 76-year-old woman having a diagnosis of diabetes mellitus had been treated surgically for two years for stage-4 diabetic ulcer on a lower extremity. Her lesion required debridement every 3 to 6 months to remove necrotic tissues. After a surgeon had declared the ulcer incurable by any means, she changed physicians and was treated with a combination of NHF5 liquid inside the wound and (as a local vasodilator to stimulate blood flow) 0.02 weight % nitroglycerin paste outside the wound, in which a wet gauze was applied directly to the wound twice a day for 20-30 minutes each time. The initial ulcer measured 1.7 inch in diameter. After the first week of treatment the edge of the ulcer showed significant improvement, with the dark color of dying tissue having been lightened. Following the second week of treatment with the wet pads the wound had shrunk and appeared to be much healthier. After three months of treatment the wound had healed completely, and the ulcer did not reappear in the three months following the treatment period.

EXAMPLE 3

Preventing Bedsore Formation

Ten bedridden elderly patients received a prophylactic treatment as follows: A batch of NHF5 was prepared as described in EXAMPLE 1 but without the mimosa extract or silver ion. Wound dressings were wet with the composition, and placed for 20-30 minutes once or twice per day on bedridden patients—and in one case on a wheelchair-bound patient—on areas of skin where bedsores were most likely to develop. The patients were turned every two hours as is normal protocol to minimize the development of bedsores. Under typical conditions in the healthcare industry 20% of the patients would have bedsores of a degree Stage II or higher when patients were turned regularly but lacked prophylactic treatment. And normally it would be quite unusual to have a patient who was bedridden for 6 years or more without developing at least one bedsore. Thus the new results summarized below are statistically and medically significant.

| Individuals | Bedridden Condition | NHF5 Treatment | Length of NHF5 Treatment | Number of Bedsores Developed |
|---|---|---|---|---|
| 01. Female, age 76 | Hip injury | Once per Day | 6 Years | None |
| 02. Male, age 81 | Cardiovascular problems | Twice per Day | 6 Months | None |
| 03. Female, age 67 | Hip injury | One-to-Two Times per Day | 3 Months | None |
| 04. Male, age 52 | Stroke | Once per Day | 27 Days during which the patient was comatose | None |
| 05. Male, age 82 | Wheelchair; severe arthritic knee | Once per Day | 12 Months | None |
| 06. Diabetic Male, age 72 | Home care patient | Once per Day | 12 Months | 1 stage 1 bedsore @ 3 months* |
| 07. Male, age 78 | Congestive heart failure | Once per Day | 2 Months | None |
| 08. Female, age 68 | Stomach cancer | Once per Day | 45 Days | None |
| 09. Female, age 68 | Brain tumor | Once per Day | 30 Days | None |
| 10. Very obese Male, age 69 | Home care patient with diabetes | Once per Day | 6 Months | 1 stage 1 bedsore & 1 diabetic ulcer @ 4 months[+] |
| | Totals for 10 patients | | ≈116 Months | 2 Stage 1 bedsores |

*The bedsore was healed in 6 days with increased physiotherapeutic procedures. No more bedsores developed.
[+]The Bedsore healed in 11 days with increased physiotherapeutic procedures. The diabetic ulcer healed in 17 Days by conventional treatment. No other bedsores or ulcers developed.

EXAMPLE 4

Treating First and Second Degree Burns

A simple spray application by the patient can be effective. The protocol involves simply spraying the composition on the damaged area of skin periodically until the burning sensation disappears. It has been found to be effective to spray whenever the patient subjectively feels the pain from the burn return. Three to five applications over a period of 45 minutes have been found to be sufficient for a minor burn, with no pain or evidence of a burn the following days. For second-degree burn, gel can be applied manually to damaged area when burn appears.

EXAMPLE 5

Treating Third Degree Burns

The severity of the burn and the percentage of skin surface involved determine whether treatment can be self-applied by the patient or administered by a physician. For highly localized burns, as with touching a frying pan, the patient can self-administer. For more extensive burns the patient should see a physician and the following regimen should be applied by the physician or clinic or under their administration.

For the more extensive burn, begin treatment with a spray application. Use the spray liberally to saturate the damaged area in order to moisturize and clean it. Do not touch the damaged area—only spray sufficiently to clean the wound. In the second stage, apply bandages soaked in the composition. Be sure to keep the bandages wet with the formula in order to prevent adhesion to the damaged epidermis. Keep soaked bandages on the wound for thirty to sixty minutes. Then remove bandages and use simple antiseptic, non-stick bandages to prevent or reduce exposure to bacterial agents. The entire procedure should be repeated every six to eight hours until skin flexibility returns, swelling is considerably reduced, and new skin formation appears. Expect normal skin texture and the virtual absence of keloidal tissue.

Progress of healing in a patient who had received third-degree burns during radiation therapy for metastatic cancer was as follows. The patient's left foot before radiation therapy or treatment by the invention method was visibly afflicted by a severe bacterial infection. The same foot after received a third-degree burn while receiving 5.8 rads of radiation. Tissue stiffening and necrosis were associated with the burn damage; treatment by the invention method had not yet been provided. At that point radiation treatment was halted and the patient's physicians recommended amputation of the foot due to the continued observation of minor metastasis in a biopsy, and due to the lost mobility of the foot due to stiffening caused by the very deep radiation burn. The patient elected instead to be treated by the invention method. The foot area was treated with a wound dressing that had been soaked in the liquid herbal mixture of the invention, in this case without the silver ion or mimosa extract, where a dressing was applied once or twice each day for about 20 to 30 minutes each time. Within two weeks' time the foot was healing. After a month of treatment by this method: the patient had regained mobility and the foot looked almost normal. A biopsy at this time found no metastatic activity in the foot; it is believed the radiation therapy itself may have been responsible for the post-radiation minor metastasis observed earlier, and that cessation of radiation accounted in this case for cessation of metastasis.

EXAMPLE 6

Treating Minor Cuts, Wounds and Abrasions

Spray the damaged area liberally to saturate the damaged area and clean the wound. Application should be repeated until bleeding is completely stopped. The gel form should now be applied and closed with simple non-stick bandages.

EXAMPLE 7

Treating Major Wounds and Surgical Incisions

Bathe wound in formula to ensure antiseptic environment and complete saturation. This should provide both sufficient antiseptic activity and substantial pain reduction. When bandaging, apply the gel form to bandage to provide catabolic activity. Expect substantially increased healing rates. Repeat regimen throughout standard bandage rotation procedures.

EXAMPLE 8

Dermal Irritation Testing

Tests in a third party laboratory for primary dermal irritation on the shaved skin of six New Zealand White rabbits by the composition with erythema and eschar and formation yielded results as follows:

| Skin Condition | Reading (Hours) | #1 | #2 | #3 | #4 | #5 | #6 | Average |
|---|---|---|---|---|---|---|---|---|
| Intact | 24 | 2 | 1 | 0 | 0 | 0 | 0 | 0.50 |
| Intact | 72 | 0 | 0 | 0 | 0 | 0 | 0 | 0.00 |
| Abraded | 24 | 1 | 0 | 0 | 0 | 0 | 0 | 0.33 |
| Abraded | 72 | 0 | 0 | 0 | 0 | 0 | 0 | 0.00 |
| | | | | | | | Subtotal | 0.83 |

Tests for primary dermal irritation on the shaved skin of six New Zealand White rabbits by the composition with edema yielded results as follows:

| Skin Condition | Reading (Hours) | #1 | #2 | #3 | #4 | #5 | #6 | Average |
|---|---|---|---|---|---|---|---|---|
| Intact | 24 | 1 | 0 | 0 | 0 | 0 | 0 | 0.17 |
| Intact | 72 | 0 | 0 | 0 | 0 | 0 | 0 | 0.00 |
| Abraded | 24 | 1 | 0 | 0 | 0 | 0 | 0 | 0.00 |
| Abraded | 72 | 0 | 0 | 0 | 0 | 0 | 0 | 0.00 |
| | | | | | | | Subtotal | 0.17 |

Total: 1.00. Primary irritation score=1.00/4=0.25.

EXAMPLE 9

Acute Oral Toxicity Testing

Third party tests for acute oral toxicity in 5 male and 5 female Sprague Dawley derived rats at a dose level of 5 g/kg body weight found LD50 exceeds 5 g/kg, and there were no mortalities or gross abnormalities observed during the 14 day test period. All animals appeared to be normal throughout the 14 day study period and at necropsy. for circulatory, respiratory, autonomic and central nervous systems, somatomotor activity, behavior patterns, onset of tremors, convulsions, salivation, lethargy, sleep and coma, skin and fur, and eyes and mucous membranes. The body weight data is shown in the following table.

| No. | Eartag # | Sex | Day 0 Initial Weight (g) | Day 7 Intermediate Weight (g) | Day 14 Final Weight (g) | Change in Weight (g) |
|---|---|---|---|---|---|---|
| 1 | 9081 | F | 227 | 270 | 285 | +58 |
| 2 | 9082 | F | 219 | 247 | 262 | +43 |
| 3 | 9083 | F | 223 | 257 | 273 | +50 |
| 4 | 9084 | F | 256 | 272 | 292 | +36 |
| 5 | 9085 | F | 231 | 260 | 274 | +43 |
| 6 | 9086 | M | 227 | 294 | 343 | +116 |
| 7 | 9087 | M | 239 | 313 | 356 | +117 |
| 8 | 9088 | M | 234 | 297 | 348 | +114 |
| 9 | 9089 | M | 249 | 318 | 370 | +121 |
| 10 | 9090 | M | 216 | 278 | 303 | +87 |

The embodiments of the invention as described herein are merely illustrative and are not exclusive. Numerous additions, variations, derivations, permutations, equivalents, combinations and modifications of the above-described composition and methods will be apparent to persons of ordinary skill in the relevant arts. The invention as described herein contemplates the use of those alternative embodiments without limitation.

I claim:

1. An aqueous topical composition comprising:
   dried aloe vera extract;
   dried passion flower extract;
   dried goldenseal extract;
   dried American ginseng extract; and
   water; and
   wherein the concentration of dried aloe vera extract ranges from 0.5% to 20% by weight of the topical composition;
   wherein the concentration of dried passion flower extract ranges from 0.05% to 4% by weight of the topical composition;
   wherein the concentration of dried goldenseal extract ranges from 0.05% to 4% by weight of the topical composition;
   wherein the concentration of dried American ginseng extract ranges from 0.1% to 8% by weight of the topical composition; and
   wherein the topical composition is a liquid.

2. The topical composition of claim 1, further comprising dried mimosa extract.

3. The topical composition of claim 2, wherein the concentration of dried mimosa extract ranges from 0.015% to 8% by weight of the topical composition.

4. The topical composition of claim 1, further comprising silver ion.

5. The topical composition of claim 4, wherein the concentration of silver ion ranges from 2 to 1,000 ppm.

6. The topical composition of claim 1, further comprising hydrogen peroxide.

7. The topical composition of claim 6, wherein the concentration of hydrogen peroxide ranges from 0.03% to 3.0% of the aggregate volume of the liquid components of the topical composition.

8. The topical composition of claim 1, further comprising an organic solvent selected from the group consisting of methanol, ethanol, iso-propanol, n-propanol, tert-butanol, sec-butanol, n-butanol, dimethylsulfoxide, n-methylformamide, 1,2,3-propanetriol, 1,2-propanediol, and 1,2-ethanediol.

9. The topical composition of claim 8, wherein the concentration of the organic solvent ranges from 2% to 50% of the aggregate volume of the liquid components of the topical composition, and wherein the concentration of water ranges from 50% to 98% of the aggregate volume of the liquid components of the topical composition.

10. An aqueous topical composition comprising:
    dried aloe vera extract;
    dried passion flower extract;
    dried goldenseal extract;
    dried American ginseng extract;
    a gelling agent; and
    water; and
    wherein the concentration of dried aloe vera extract ranges from 0.5% to 20% by weight of the topical composition;
    wherein the concentration of dried passion flower extract ranges from 0.05% to 4% by weight of the topical composition;
    wherein the concentration of dried goldenseal extract ranges from 0.05% to 4% by weight of the topical composition;
    wherein the concentration of dried American ginseng extract ranges from 0.1% to 8% by weight of the topical composition; and
    wherein the topical composition is a gel.

11. The topical composition of claim 10, wherein the gelling agent is selected from the group consisting of gelatin, guar gum, carrageenan, polyethylene oxide, methyl cellulose, and hydroxypropylmethyl cellulose.

12. The topical composition of claim 10, further comprising dried mimosa extract.

13. The topical composition of claim 12, wherein the concentration of dried mimosa extract ranges from 0.015% to 8% by weight of the topical composition.

14. The topical composition of claim 10, further comprising silver ion.

15. The topical composition of claim 14, wherein the concentration of silver ion ranges from 2 to 1,000 ppm.

16. The topical composition of claim 10, further comprising hydrogen peroxide.

17. The topical composition of claim 16, wherein the concentration of hydrogen peroxide ranges from 0.03% to 3.0% of the aggregate volume of the liquid components of the topical composition.

18. The topical composition of claim 16, wherein the gelling agent is selected from the group consisting of gelatin, guar gum, carrageenan, polyethylene oxide, methyl cellulose, and hydroxypropylmethyl cellulose.

19. The topical composition of claim 10, further comprising an organic solvent selected from the group consisting of methanol, ethanol, iso-propanol, n-propanol, tert-butanol, sec-butanol, n-butanol, dimethylsulfoxide, n-methylformamide, 1,2,3-propanetriol, 1,2-propanediol, and 1,2-ethanediol.

20. The topical composition of claim 19, wherein the concentration of the organic solvent ranges from 2% to 50% of the aggregate volume of the liquid components of the topical composition, and wherein the concentration of water ranges from 50% to 98% of the aggregate volume of the liquid components of the topical composition.

* * * * *